United States Patent [19]
Servos

[11] 3,946,723
[45] Mar. 30, 1976

[54] ELECTRODE SWITCHING ADAPTER FOR VERTICAL RECORDING OF ELECTRONYSTAGMOGRAPHS

[75] Inventor: Gerald H. Servos, Glen Ellyn, Ill.
[73] Assignee: Instrumentation & Control Systems, Inc., Addison, Ill.
[22] Filed: Dec. 5, 1974
[21] Appl. No.: 529,808

[52] U.S. Cl............ 128/2.1 M; 346/33 ME; 346/62
[51] Int. Cl.² .......................................... A61B 5/05
[58] Field of Search........... 128/2.1 R, 2.1 M, 2.1 B, 128/2.1 Z, 2 S, 2 N, 2 T, 2.06 G; 346/33 ME, 62

[56] References Cited
UNITED STATES PATENTS

| | | | |
|---|---|---|---|
| 3,000,271 | 9/1961 | Harvey et al.................... | 128/2.1 M |
| 3,195,533 | 7/1965 | Fischer............................. | 128/2.1 B |
| 3,217,706 | 11/1965 | Sullivan........................... | 128/2.1 M |
| 3,699,948 | 10/1972 | Ota................................... | 128/2.06 G |
| 3,721,230 | 3/1973 | Ziernicki......................... | 128/2.1 B |
| 3,875,930 | 4/1975 | Silva et al....................... | 128/2.1 B |

OTHER PUBLICATIONS
Grieco, "New Apparatus . . . Physiology," Med. & Biol. Eng., Vol. 9, No. 6, pp. 705-710, 1971.

Primary Examiner—Robert W. Michell
Assistant Examiner—Lee S. Cohen
Attorney, Agent, or Firm—Alter and Weiss

[57] ABSTRACT

A switching adapter that provides a rapid and convenient apparatus for selective recording of vertical eye movements with a single channel recorder in electronystagmograph apparatus. A number of single channel recorders are used in the field to observe the horizontal eye movements elicited by thermally induced vestibular unbalance. In certain types of pathological unbalances, vertical eye movement is also present, therefore, it is highly desirable to be able to also record the vertical eye movement. The switching adapter conveniently converts single channel recorders that are normally used for recording horizontal eye movement for recording vertical nystagmus.

8 Claims, 1 Drawing Figure

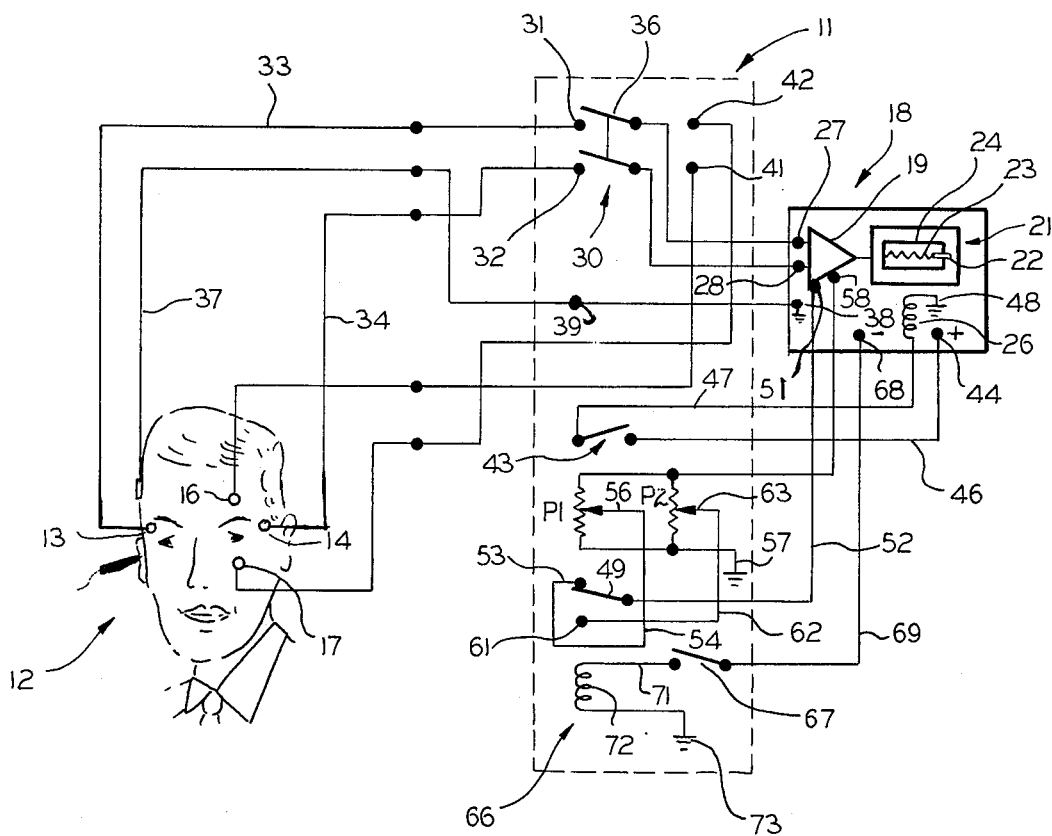

ELECTRODE SWITCHING ADAPTER FOR VERTICAL RECORDING OF ELECTRONYSTAGMOGRAPHS

This invention relates to apparatus used for measuring nystagmus, and more particularly, to electrode switching adapters for recording vertical movement of the subject's eye with a single channel recorder during electronystagmograph tests.

The phenomenon known as nystagmus is widely used to detect vestibular disorders. There is apparatus presently available which records the relative position of the patient's eyeballs under conditions of induced or spontaneous nystagmus.

Nystagmus may be induced by many known methods. This invention is not concerned with the method of inducing nystagmus; but is concerned with the apparatus utilized in recording the velocity of the movement of the eyeball. The invention is especially concerned with apparatus for adapting a single channel recorder for recording both the horizontal movements of the eyeball which are normally recorded, and in addition, for recording the less frequently recorded vertical movements of the eyeballs under nystagmus conditions.

To make the recording, electrodes are attached to the patient. A first set of electrodes is normally attached to the temples of the patient, for detecting the cornea-retina potential. The horizontal movement of the eyeball varies the magnitude and polarity of the voltage reaching the electrodes on each temple. These variations are translated by the recorder to show the horizontal movement of the patient's eyeball.

A second pair of electrodes are fastened above and below the patient's eye. For example, an electrode may be attached just above the brow of the left eye of the patient, and a second electrode of the second pair of electrodes attached to the left cheek bone below the left eye of the patient. The cornea-retina potential differences are measured through the second set of electrodes to determine the vertical position of the patient's eyeball.

If a two channel recorder is available as part of the electronystagmograph equipment, then there is no problem in recording both the horizontal and vertical movement of the eyeball. However, in may cases, there is only a single channel recorder available.

In the past to record the vertical movement of the eyeball, as well as the horizontal movement, nystagmus is induced with the electrodes which detect the horizontal movement of the eyeball connected to the single input of the recorder. After the horizontal movement is recorded, the nystagmus inducing procedure is repeated with the vertical electrodes connected to the single channel recorder. Obviously, with this type of procedure, the patient must be subjected to the nystagmus inducing procedure for a greater length of time with all of the inherent discomfitures. Further, the operator must remember to mark the recording paper so that when analysis is later made, it is readily discernible which are the vertical recordings and which are the horizontal recordings.

Another fault with the presently available way of recording the vertical eye movement is that the operator must remember to readjust the gain of the amplifier, since the vertical indications are much smaller than the horizontal indications; therefore, the gain must be increased to get meaningful recordings.

Accordingly, an object of the present invention is to provide electrode switching adapter means for enabling recordings of the horizontal and vertical eyeball movement with induced nystagmus utilizing a single channel recorder.

A related object of the present invention is to provide electrode switching adapters which automatically indicate when the vertical eyeball movement is being recorded.

Yet another object of the present invention is to provide an automatic gain control to automatically calibrate the vertical and horizontal channels to account for the scale factors between the vertical movement and the horizontal movement of the eyeball under induced nystagmus.

Yet another object of the present invention is to provide electrode switching adapters for adeptly switching between vertical and horizontal electrodes placed on the patient during nystagmus testing.

In accordance with one aspect of this invention an electrode switching adapter is used in the connection between two pairs of cornea retina potential detecting electrodes and a recorder used in measuring induced nystagmus. A first pair of electrodes are placed so as to detect the horizontal movement of the patient's eye during nystagmus testing. A second pair of electrodes is placed so as to detect vertical movement of the eye during nystagmus testing. The adapter comprises a simple four-pole, double-throw switch used to connect either the vertical or the horizontal electrodes into the input of the recorder.

Means are also provided for automatically placing a mark on a recorder which indicates that the vertical eye movements are being recorded. Further, means are provided for automatically changing the gain of the recorder amplifier to account for the different scale of readings obtained between vertical movements and horizontal movements during nystagmus testing.

The above mentioned and other objects and features of this invention will become more apparent from a description of the apparatus in the following specification taken in conjunction with the following schematic drawing of the electroswitching adapter shown used to selectively interconnect one of the pairs of electrodes applied to the patient and the recorder.

Turning now to the drawing, the electrode switcing adapter apparatus is generally shown at 11, bordered by the dashed lines. The patient is indicated at 12 and is shown with means for detecting both horizontal and vertical eyeball movement under nystagmus conditions attached to him. More particularly, there is shown a pair of electrodes for detecting the horizontal eyeball movements, such as electrodes 13 and 14, attached to the opposite temples of the patient. Similarly, there is shown a second pair of electrodes 16 and 17 attached to the brow and cheek bones of the patient, respectively, proximate to the patient's left eye, for example. The middle electrode is a common ground.

The recorder is shown at block 18. The interior of the block is shown as including amplifying means, such as amplifier 19, which leads into the actual recording mechanism 21. The recording mechanism 21 includes a pen 22 which makes a mark, such as mark 23, on paper 24 as the paper moves past the pen. The equipment further includes means, such as marker pen coil 26, for marking an indication in the recording paper that the vertical sensing electrodes are in use.

As is obvious, the recorder 18 is a single channel recorder. Prior to the use of adapter 11, the horizontal movement of the eyeball was detected through the first pair of electrodes, such as electrodes 13 and 14, attached to the input terminals 27 and 28 of the recorder, connected directly to the input of amplifier 19.

Subsequent to the horizontal eyeball movement testing, nystagmus was again induced in the patient with the horizontal electrodes 13 and 14 disconnected and the vertical electrodes 16 and 17 connected in their place. Either a preamplifier was also connected or the gain of the amplifier was adjusted to record the smaller vertical movement signals with the necessary amplitude on the chart paper 24.

With adapter 11 both the horizontal movement detecting electrodes 13 and 14 and the vertical movement detecting electrodes 16 and 17 are connected directly to the adapter 11. More particularly, the horizontal movement detecting electrodes 13 and 14 are connected to poles, such as poles 31 and 32, of means such as double-pole, double-throw switch 30 through conductors 33, 34 respectively. The armature 36 of the switch is connected directly to terminals 27 and 28 of recorder 18. A grounding connection is also made through conductor 37 directly to a ground terminal 38 on the recorder, or the ground connection can go to a terminal 39 in the adapter unit and then from there to terminal 38 of the recorder.

When during the test the examiner or the doctor wishes to observe the vertical movements, the armature 36 is moved to make contact with poles 41 and 42 connected respectively to electrodes 16 and 17 proximate to the patient's eyes for the detection of the vertical movement. The armature of the double-pole, double-throw switch is still connected to the input terminals 27 and 28 of amplifier 19 on the recorder 18.

Means are provided for causing the recorder to indicate that the vertical readings are being recorded. More particularly, as shown herein there is a switch 43 usually mechanically interconnected with switch 36 which is connected between a marker pen coil 26 and positive potential in the recorder at 44. When switch 43 is closed, a circuit is completed between positive potential 44 through conductor 46, switch 43, conductor 47, and through marker pen coil 26 to ground at 48. This causes a new current to flow through the coil, and change in current results in making a mark which is readily interpreted as indicating vertical readings.

Means are further provided for varying the gain of amplfier 19 as a function of whether the horizontal readings are being taken or the vertical readings are being taken. More particularly, when the horizontal readings are being taken, then switch 49 is in its normal position, wherein it is attached to potentiometer P1. Then, a circuit extends from a signal source in the recorder amplifier, indicated at 51, through conductor 52, switch 49 connected to pole 53, through conductor 54 to wiper 56 connected to potentiometer P1. One end of the potentiometer is connected to ground at 57 while the other end of the potentiometer is connected to the gain control terminal 58 of amplifier 19.

When switch 30 is controlled to connect the vertical electrode to the amplifier, then the armature of switch 49 is moved to make contact with pole 61 of the double-pole, single-throw switch, thereby connecting the potentiometer P2 into the circuit. More particularly, the circuit then extends from the signal source terminal at 51 through conductor 52, the armature of switch 49, pole 61, conductor 62, to the wiper 63 of the potentiometer P1 to the gain control terminal 58. The values of the potentiometer P1 and P2 are such that the proper gains are provided by amplifier 19 to accomodate the different signal levels when detecting the horizontal movement of the eyeball, as opposed to the vertical movement of the eyeball.

Means are provided for interconnecting and coordinating the operation of switches 49, 43 and 30. More particularly, these switches are preferrably relay contacts on relay 66. Relay 66 is energized responsive to the operation of single-pole, single-throw switch 67 which is preferrably interconnected with switch 30. Switch 67 controls the circuit that extends from negative potential at 68 in the recorder through conductor 69, single-pole, single-throw switch 67, conductor 71, relay coil 72 to ground 73. Thus, when switch 67 is operated to the closed position, then the coil of relay 66 is energized and armatures 49 and 43 of the relay are operated to connect both the pen control circuit including the coil 26 and the gain control circuit, including the potentiometers P1 and P2.

Thus, in operation the operator of the electronystagmograph equipment can easily obtain either horizontal or vertical readings as desired.

Thermal fluid carrying means (not shown) are used to induce nystagmus in the patient. The operator then moves switch 30 to connect the first pair of electrodes 13, 14 to inputs 27, 28 of amplifier 19 in recorder 18. The gain of the amplifier is set over the circuit that extends from positive potential at 51 through conductor 52, contacts 49 and 53 on relay 66, wiper 56 of potentiometer P1, and through that potentiometer to input 58 of the amplifier. The recorder makes a record of the horizontal eye movements.

The operator moves the armature 36 of switch 30 to connect the second pair of electrodes 16, 17 to the input of the recorder. The recorder now records the vertical eye movements. Moving armature 36 to connect the second pair of electrodes closes switch 67 to energize relay 66. The energization of relay 66 disconnects potentiometer P1 and connects potentiometer P2 to control amplification of amplifier 19 for the smaller vertically initiated potentials. The operated relay also completes the circuit to energize coil 26 and mark the record to note that the vertical readings are being recorded.

While the principles of the invention have been described above in connection with specific apparatus and applications, it is to be understood that this description is made only by way of example, and not as a limitation on the scope of the invention.

I claim:

1. An electronystagmographic testing system for testing and recording nystagmus,
said electronystagmographic system comprising a
first pair of electrodes attachable to a patient to detect signals responsive to the horizontal movement of the patient's eye,
a second pair of electrodes attachable to the patient to detect the vertical movement of the patient's eye,
single channel recording means for providing a trace indicating the eye movements of the patient,
input terminals on said recording means, said trace being responsive to said detected signals received at the said input terminals, an electrode switching adapter for selectively recording vertical eye movements or horizontal eye movements on said single channel recording means, said electrode switching adapter comprising first switching means for selectively attaching either said first or said second pair of electrodes to the input terminals of said recording means, said first switching means having first pole means attached to said first pair of electrodes and second pole means attached to said second pair of electrodes, armature means on said first switching means for connecting to said first pole means or said second pole means and attached to the input terminals of said single channel recording means, whereby said single channel recording means records either the horizontal or the vertical movement of the eye depending on whether the armature means is connected to said first pole means or said second pole means, respectively, said single channel recording means including amplifier means, for amplifying the detected signals to provide said trace, means for coupling said input terminals to the input of said amplifier means, and amplifier gain varying means in said switching adapter for automatically varying the gain of the amplifier means depending on whether the horizontal or vertical eye movements are being recorded.

2. An electronystagmographic testing system for testing and recording nystagmus, said electronystagmographic system comprising a first pair of electrodes attachable to a patient to detect the horizontal movement of the patient's eye, a second pair of electrodes attachable to the patient to detect the vertical movement of the patient's eye, single channel recording means for providing a trace indicating the eye movements of the patient, input terminals on said recording means, said trace being responsive to signals received at the said input terminals, an electrode switching adapter for selectively recording vertical eye movements or horizontal eye movements on said single channel recording means, said electrode switching adapter comprising first switching means for selectively attaching either said first or said second pair of electrodes to the input terminals of said recording means, said first switching means having first pole means attached to said first pair of electrodes and second pole means attached to said second pair of electrodes, armature means on said first switching means for connecting to said first pole means or said second pole means and attached to the input terminals of said single channel recording means, whereby said recording means records either the horizontal or the vertical movement of the eye depending on whether the armature means is connected to said first pole means or said second pole means, respectively, said recording means including amplifier means for amplifying the detected signals to provide said trace, means for coupling said input terminals to the input of said amplifier means, amplifier gain varying means in said switching adapter for automatically varying the gain of the amplifier means depending on whether the horizontal or vertical eye movements are being recorded, said amplifier gain varying means comprising first and second resistor means, and second switching means for attaching said first resistor means to control the gain of the amplifier means when said first pair of electrodes are attached to the input terminals and for attaching said second resistor means when said second pair of electrodes is attached to the input terminals.

3. The electrode switching adapter of claim 2 wherein said second switching means comprises a relay, said relay being unoperated when said first pair of electrodes are attached to the input of said recording means, and means for energizing said relay when said second pair of electrodes are attached to said recording means.

4. The electrode switching adapter of claim 3 wherein said means for energizing said relay comprises a third switching means attached to said first switching means to be operated when said first switching means connects said second pair of electrodes to the input terminals of said recording means, and means responsive to the energization of said relay means for disconnecting said first resistor means, and connecting said second resistor means to control the gain of the amplifier means.

5. An electronystagmographic testing system for testing and recording nystagmus, said electronystagmographic system comprising a first pair of electrodes attachable to a patient to detect signals indicating horizontal movement of the patient's eye, a second pair of electrodes attachable to the patient to detect signals indicating vertical movement of the patient's eye, single channel recording means for providing a trace indicating the movement of the patient's eye, input terminals on said recording means, said trace being provided responsive to signals received at the input terminals, an electrode switching adapter for selectively recording either the vertical eye movement or the horizontal eye movement on said single channel recording means, said electrode switching adapter comprising first switching means for selectively attaching either said first or said second pair of electrodes to the input terminals of said recording means, said first switching means having a first pole means attached to said first pair of electrodes and second pole means attached to said second pair of electrodes, armature means on said first switching means for connecting to said first pole means or said second pole means and attached to the input terminals, whereby said single channel recording means records either the horizontal or the vertical movement of the eye depending on whether the armature means is connected to said first pole means or to said second pole means, respectively, said recording means including means for leaving a trace on moving paper, said trace being a function of the signals at the input terminals of said recording means, means comprising coil means for moving said means for leaving the trace, and second switching means for changing the current to said coil means responsive to said first switching means being operated to connect said second pair of electrodes to the input terminals of said recording means, whereby said means for leaving the trace moves responsive to the connection of said second pair of electrodes to the input terminals of said recording means.

6. The electrode switching adapter of claim 5 wherein said recording means includes amplifier means for amplifying the detected signals to provide said trace, means for coupling said input terminals to the input of said amplifier means, and means are provided for varying the gain of the amplifier means depending on whether said first set of electrodes is connected to the input terminals of said recording means or whether said second pair of electrodes are connected to the input terminals of said recording means.

7. The electrode switching adapter of claim 6 wherein said means for varying the gain of the amplifier means comprises a first potentiometer, a second potentiometer, and relay means for connecting said first potentiometer to control the gain of the amplifier means when said first pair of electrodes is connected to the input terminals of the recording means and disconnecting said first potentiometer, while connecting said second potentiometer to control the gain of the amplifier means when the second pair of electrodes is connected to the input terminals of the recording means.

8. The electrode switching adapter of claim 7 wherein said relay means is in a nonenergized condition when said first pair of electrodes are connected to the amplifier means, third switching means for energizing said relay means when the second pair of electrodes is connected to the input terminals of the recording means, and contact means or said relay means operated responsive to the energization of said relay means for disconnecting said first potentiometer and connecting said second potentiometer to control the gain of the amplifier means.

* * * * *